United States Patent [19]

Fini

[11] Patent Number: 4,951,503
[45] Date of Patent: Aug. 28, 1990

[54] METHOD AND APPARATUS FOR DETERMINING THE HEATING VALUE OF A GASEOUS FUEL

[75] Inventor: Anselmo Fini, Syracuse, N.Y.

[73] Assignee: Niagara Mohawk Power Corporation, Syracuse, N.Y.

[21] Appl. No.: 469,012

[22] Filed: Jan. 23, 1990

[51] Int. Cl.[5] ..................... G01N 30/78; G01N 33/22
[52] U.S. Cl. .................................................. 73/23.1
[58] Field of Search ................... 73/23.1; 374/36; 422/89, 98; 364/497

[56] References Cited

U.S. PATENT DOCUMENTS

| | | |
|---|---|---|
| 3,291,980 | 12/1966 | Coates et al. |
| 3,479,798 | 11/1969 | Ryhage. |
| 3,566,674 | 3/1971 | Talroze et al. ........................ 73/23.1 |
| 4,229,968 | 10/1980 | Muldoon ............................... 73/23.1 |
| 4,246,773 | 1/1981 | Haruta ..................................... 73/24 |
| 4,345,463 | 8/1982 | Wilson et al. ..................... 73/23.1 X |
| 4,355,533 | 10/1982 | Muldoon ............................... 73/23.1 |
| 4,553,985 | 11/1985 | Dahlgren et al. ............... 73/23.1 X |

OTHER PUBLICATIONS

"Gas Flow Measurement: Practical Aspects and Research Results", presented at Jun., 1988, IGT Meeting on Natural Gas Energy Measurement by Mr. Norman F. Mease.
"Densitometer and Chromatograph Energy Measurement-A CNG Transmission Perspective", presented at Jun. 1988, IGT Meeting on Natural Gas Measurement by Mr. J. M. Dowdell.
"High-Speed Analysis and BTU Monitoring of Natural Gas", presented at Jun. 1988, IGT Meeting on Natural Gas Energy Measurement by Mr. Curtis A Ray.
"A Dual Channel Gas Analyzer Based on Capillary Technology", presented at Jun. 1988, IGT Meeting on Natural Gas Energy Measurement by Dr. Winfred Sanders.
"Acoustic Measurement for Gas BTU Content", J. W. Watson & F. A. White, published Oil & Gas Journal—Technology, Apr. 5, 1982.

Primary Examiner—John Chapman
Assistant Examiner—Joseph W. Roskos
Attorney, Agent, or Firm—Heslin & Rothenberg

[57] ABSTRACT

A method and apparatus are described for determining the heating value of natural gas. The apparatus utilizes a chromatographic column, and a first sensor connected by a length of tubing in series with a second sensor, all of which are placed in a thermally isolated chamber, in order to keep the temperature constant. The method operates on a principle of comparison of the mass of natural gas, which contains hydrocarbons, higher hydrocarbons, and noncombustibles, with the mass of pure methane. In determining the heating value of the natural gas, the amount of noncombustibles present in the natural gas is determined, and this amount is subtracted from the mass of the natural gas to yield the mass of the hydrocarbon content. From the mass of the hydrocarbon content, the amount of higher hydrocarbons in the natural gas is determined. Once this is complete, the amount of methane present in the natural gas is calculated and that value along with the value representative of the higher hydrocarbon content are used to calculate the heating value of the natural gas.

21 Claims, 2 Drawing Sheets

METHOD AND APPARATUS FOR DETERMINING THE HEATING VALUE OF A GASEOUS FUEL

BACKGROUND OF THE INVENTION

1. Field of the Invention

This invention relates generally to the field of measuring instruments and, more particularly, to a process and apparatus for determining the heating value per unit volume of a gaseous fuel, such as natural gas.

2. Background Information

Conventionally, gaseous fuel is sold on the basis of its heating value or net heat content. Measurement of the heating value of a distributed fuel, such as natural gas, is typically accomplished by testing a sample of the gas in a laboratory utilizing complex and expensive instruments.

For example, it is now necessary for a person employed by a gas company to physically go to a gas source location or custody transfer station, take a sample of the gas being distributed and then return to the laboratory to determine its heating value. In the laboratory, two methods are most frequently used to obtain an accurate measure of heating value: combustion calorimetry, and chromatography along with a thermal conductivity detector.

Combustion calorimetry involves the burning of a partial stream of the combustible gas with an open flame or with a catalyst and measuring the heat produced. This procedure requires frequent maintenance of the apparatus since a flame can change due to deposits of combustion residues or because a combustion catalyst gradually declines in effectiveness.

Alternatively, a chromatograph along with a thermal conductivity detector is sometimes employed for determining the heating value of a fuel gas. After the sample is taken, a known amount of gas is introduced into the inlet of the chromatographic column. Typically, helium is used as the carrier gas, and as the column elutes each component of the gas, the thermal conductivity detector measures the changes in the thermal conductivity of the gas stream. The quantity of each of the constituents of the fuel gas is determined from these changes in thermal conductivity by a comparison to the changes produced by known quantities of the constituents. Since the heating value of each constituent is known, the total heating value of the gaseous fuel may be computed.

Both of these methods must be applied in a well-defined, controlled environment. The need for such an environment, along with the need to collect and transport samples and for complex measurement apparatus, obviously increases the cost of determining the heating value of the gas significantly.

To summarize, current methods used to determine heating value of a fuel gas are very costly, laborious and complex. Thus, a need exists for a process and apparatus for accurately measuring the heating value of a gaseous fuel such as natural gas, which is relatively simple, low cost and, preferably, applicable to unattended field operations. The need for an economical heat value meter suitable for unattended field type installations is particularly great when a distribution system is supplied by two or more gas sources. When multiple gas sources are involved, it is necessary to take measurements at many key points in the gas distribution system in order to ensure the accuracy of customer billing. With presently available methods, this is economically impractical.

SUMMARY OF THE INVENTION

The primary object of the present invention is to provide a process and apparatus capable of determining the heating value of a gaseous fuel in a simpler, and more economical manner than with previously known methods.

Another object of the present invention is to provide a process and apparatus for determining the heating value of natural gas in an on-line manner.

A further object of the present invention is to provide a process and apparatus for determining the heating value of natural gas without combustion.

The foregoing and other object are accomplished in accordance with the present invention by a principle of comparing the mass of natural gas to the mass of a reference gas, e.g., pure methane, under the same conditions of temperature and pressure. The heat content of a natural gas which is entirely composed of hydrocarbons is proportional to the mass of the natural gas. However, most natural gases are not composed entirely of hydrocarbons, but also contain small amounts of noncombustibles, such as nitrogen and carbon dioxide, which introduce an error into the determination of the heating value. Therefore, it is important to determine the amount of noncombustibles in the natural gas so that the determined amount is not used in the determination of the heating value.

In a preferred process embodiment of the invention, a chromatographic column and two mass sensors connected in series are used to determine the heating value of natural gas. The two mass sensors are initially purged with a reference gas, e.g., methane, and then, natural gas is allowed to flow through the heat content meter bypassing the chromatographic column. At the point in the flow when the natural gas reaches the first mass sensor, methane is still present at the second mass sensor. Readings are taken at both mass sensors and these values are used to determine the mass of the natural gas.

Next, the chromatographic column and the two mass sensors are purged with methane. Then, the natural gas is permitted to flow through the chromatographic column. The particular column selected elutes various gas mixtures from the natural gas. First, a mixture of methane and nitrogen, a first noncombustible constituent gas, e.g., is eluted. This mixture flows from the outlet of the chromatographic column to the inlet of the first mass sensor. At this instance, methane is present at the second mass sensor, and a reading is taken at both mass sensors. These values are used to determine the mass of the methane and nitrogen mixture. This mass is then used to determine the mole fraction of nitrogen, which is a noncombustible. Next, the determined mass of the natural gas and the mole fraction of nitrogen are used to determine the mass of the hydrocarbons. This mass is then used to determine the heating value of the natural gas.

In an enhanced embodiment, the chromatographic column elutes a mixture of methane, nitrogen and a second noncombustible constituent gas, i.e., carbon dioxide. Again, this mixture flows from the outlet of the chromatographic column to the inlet of the first mass sensor, which forces the methane and nitrogen mixture to flow from the first mass sensor to the second mass sensor. At this point, readings are taken at both mass sensors and these readings are used to determine the mass of the methane, nitrogen, and carbon dioxide mixture. This mass, along with the mass of the methane and nitrogen mixture, is used to determine the mole fraction of carbon dioxide.

An apparatus for determining the heating value of natural gas includes a chromatographic column, a first mass sensor connected in series by a length of tubing to a second mass sensor, and control means for selectively controlling the operations of the apparatus. Additional embodiments of the process and apparatus of the present invention are described below.

BRIEF DESCRIPTION OF THE DRAWINGS

The subject matter which is regarded as the invention is particularly pointed out and distinctly claimed in the concluding portion of the specification. The invention, however, both as to apparatus and process, may best be understood by reference to the following detailed description of certain preferred embodiments thereof taken in conjunction with the accompanying drawings in which:

DETAILED DESCRIPTION OF THE INVENTION

This invention relates to a process and apparatus for advantageously determining the heating value per unit volume (BTU/ft$^3$) of a continuous flow of a gaseous fuel, e.g., natural gas, in unattended field operations. In one embodiment of the process, pure methane is used as a carrier gas through a chromatographic column and as a comparison or reference gas used in determining the mass of the natural gas. The specifics of this process will be discussed later. One embodiment of the measurement apparatus, constructed in accordance with the principles of the present invention and generally denoted (8), is represented in FIG. 1.

Figure 1:
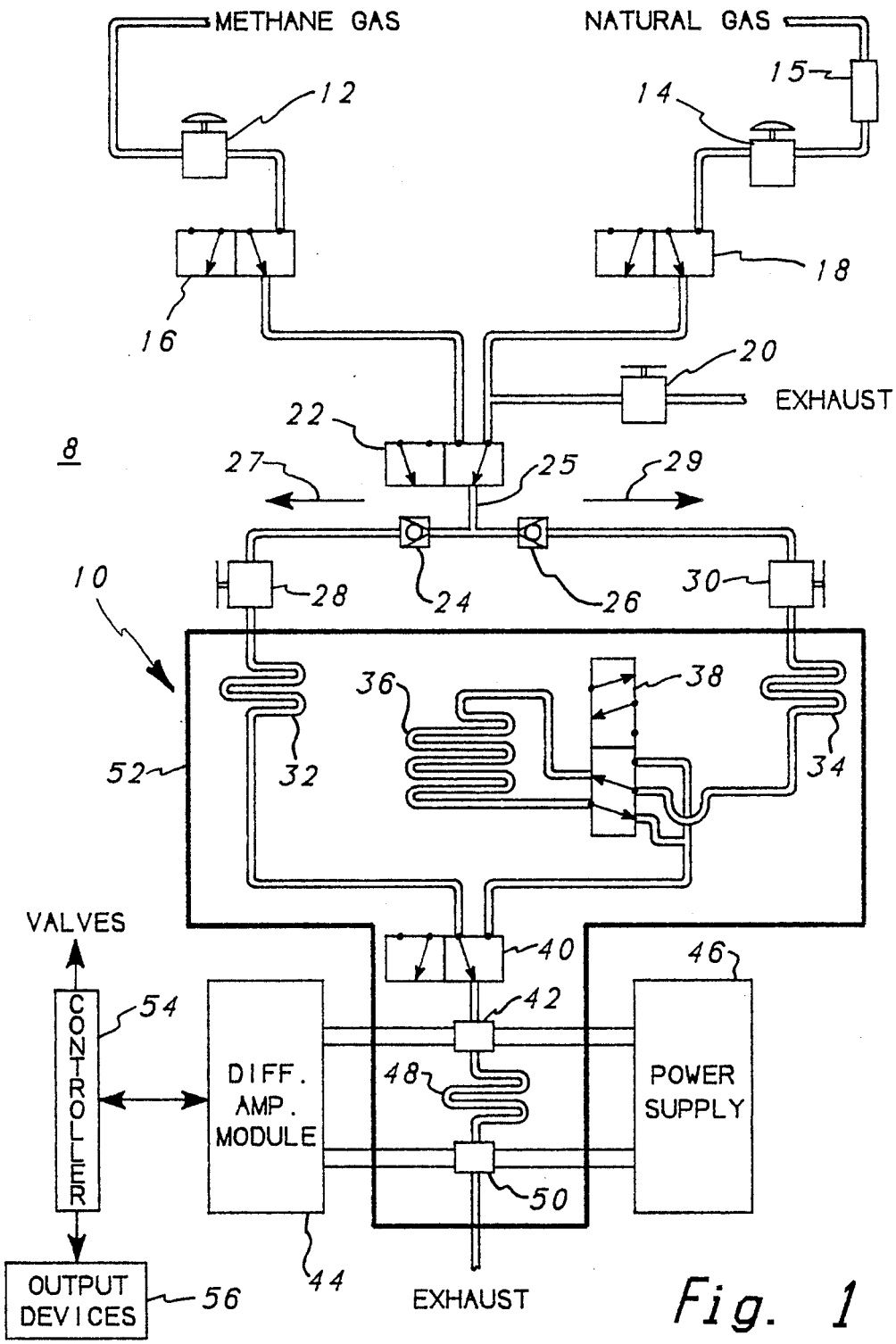
FIG. 1 is a simplified block diagram of apparatus for measuring the heating value of natural gas, constructed in accordance with the principles of the present invention.

Referring to FIG. 1, the flow paths taken by methane and a natural gas through measurement apparatus (8) will now be described. Pure methane from a source (not shown) flows through a pressure regulator (12), which is utilized to reduce the pressure of the methane to the operating pressure of the heat content meter (10). The output of this pressure regulator (12) is connected to a two-way valve (16), which is used to control the flow of methane to the inlet of a three-way valve (22).

Natural gas from a source such as a natural gas distribution line (not shown), first passes through a filter (15), which is used to remove any foreign matter and water from the natural gas. The output of this filter (15) is connected to a pressure regulator (14), which, again, is used to reduce the pressure of the natural gas to the operating pressure of the heat content meter (10). The output of this pressure regulator (14) is connected to a two-way valve (18), which is used to control the flow of natural gas to the inlet of the three-way valve (22).

The filter (15) is, for example, a gas purifier model No. N-01418-50 and available from Cole-Palmer Instrument Company of Chicago, Ill. Suitable pressure regulators (12 and 14) are also commercially available from Cole-Palmer Instrument Company.

As mentioned above, the outputs of both two-way valves (16 and 18) are connected to a three-way valve (22). This valve permits the flow of either methane or natural gas to the inlet of the heat content meter (10).

The output of valve (22) is connected through a T junction (25) to two one-way valves (24 and 26), which prevent residual gas in the meter tubing from diluting the methane or the natural gas when the three-way valve (22) switches from one gas to the other. From T junction (25) two separate flow paths are available.

A first path (27) extends through the one way valve (24) to a needle valve (28), which is used to set and equalize the flow rate of the gas along this path. The needle valve is connected to the output of one way valve (24) and to the input of a length of tubing (32). Tubing (32) is used to bring the temperature of the flowing gas which passes therethrough to that of a desired value maintained by a surrounding isothermal chamber (52). The output of the tubing (32) is connected to three-way valve (40).

A second path (29) extends through one way valve (26) to a needle valve (30). This needle valve has the same function as the above-mentioned needle valve (28) and is similarly connected to a length of tubing (34), which is also used to bring the temperature of the flowing gas which passes through the tubing to that of the isothermal chamber. However, along this second path (29) the output of tubing (34) is connected to a five way valve (38). This five way valve (38) allows the flow of gas to traverse a chromatographic column (36) in either direction. The chromatographic column (36) is preferably a Porapak QS chromatographic column which can be used to selectively elute various constituents of natural gas. The preferred column is six feet long by one-/eighth inch O.D. and is commercially available from The Anspec Company, 50 Enterprise Drive, P.O. Box 7730, Ann Arbor, Mich. 48107. The eluted constituents pass through the five way valve (38) to three way valve (40).

In one actual implementation, all the valves (16, 18, 20, 22, 24, 26, 28, 30, 40) are commercially available from Honeywell Skinner Valve Division, 95 Edgewood New Britian, Conn. 06051; or Automatic Switch Company (ASCO), 50-56 Hanover Road, Florham Park, N.J., 07932 as examples. The isothermal chamber (52) can consist of aluminum walls approximately one quarter inch thick with foam insulation. The contents of the chamber are allowed to follow the ambient temperature. However, due to the high thermal capacity of the aluminum walls and the high resistance to thermal flow of the surrounding thermal insulation, the changes in the temperature of the chamber will be very slow. Since the period needed to take the mass readings is a matter of seconds, for all practical purposes the temperature of the chamber can be considered constant during this period.

Three way valve (40) permits the flow of either methane or natural gas or its constituents (as described further below) from either flow path (27) or (29) of heat content meter (10) to a first mass sensor (42). First mass sensor (42) is connected in series by a length of tubing (48) to a second mass sensor (50). The length of tubing (48) provides a time delay, which is advantageously used in the processing discussed below, for the gas flowing through the first mass sensor to reach the second mass sensor (e.g., thirty seconds). The two mass sensors, preferably microbridge airflow sensors, type AWM2100V, measure, e.g., specific heat (which is the amount of heat necessary to raise a known quantity of gas one degree and which is substantially proportional to the mass of a gas) and are available from Micro Switch, a division of Honeywell, Inc., Freeport, Ill. For more information on these sensors, see an article by Jerry Lyman entitled "How Micro Switch's New Kind of Air-Flow Sensor Does It" published in Electronics Oct. 1, 1987 edition at page 85, which is incorporated herein, by reference. The sensors receive their power from electric power supplies (46) and the outputs of the mass sensors (42 and 50) are processed by means of electronic circuits in instrument amplifiers (44). Instrument amplifiers (44), type LH0036C, are available through National Semiconductor Corp., Santa Clara, Calif. and the integrated components for the power supplies, are commercially available from, for example, National Semiconductor Corp. or Texas Instruments, Corporate Headquarters Dallas, Tex.

Operation of heat content meter (10), including switching of the and implementation of the calculations for determining the heating value of natural gas are accomplished and controlled in an online manner by a controller (54), such as an 80C88 based microprocessor with CMOS circuitry, which is commercially available through Harris Corporation, Computer Systems Division, Ft. Lauderdale, Fla. Connected to controller (54) are conventional output devices (56), such as read out and modem devices. A typical readout device is model Q9000A, which is available through Newport Electronics, Inc., of Santa Ana, Calif., and a typical modem is Smartmodem 2400, which is available through Hayes Microcomputer Products, of Atlanta, Ga.

Figure 2:
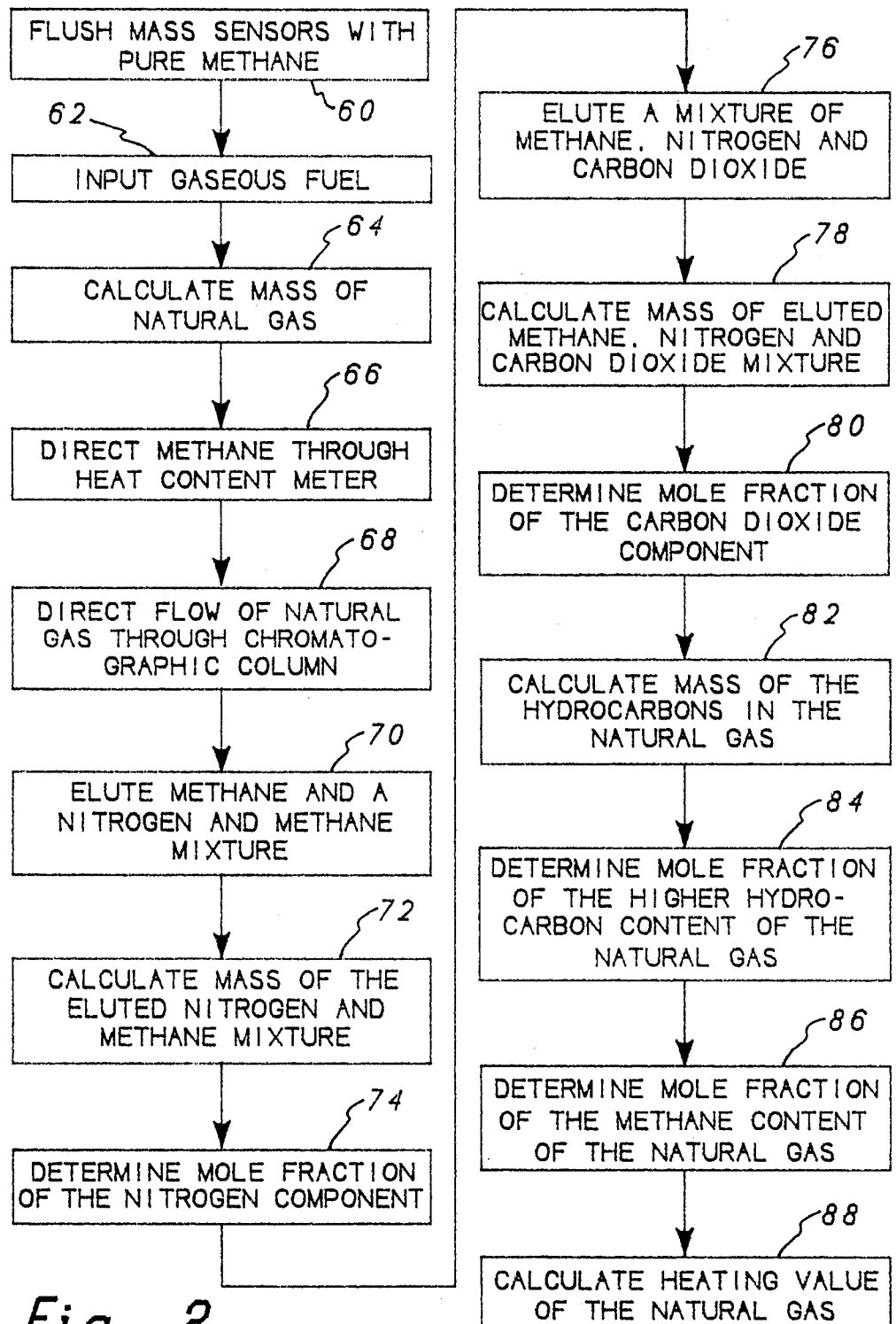
FIG. 2 presents an operational overview of a preferred method of the present invention.

Referring now to FIGS. 1 and 2, one generalized procedure for determining the heating value of a natural gas, in accordance with the principles of the present invention, will initially be summarized and then described in detail below.

Initially, the mass sensors (42) and (50) are flushed with methane (operation 60), in order to determine the operating characteristics of the sensors. Then, natural gas will be permitted to flow through the heat content meter along the first flow path (27) (operation 62). When the natural gas reaches the first mass sensor (42), pure methane will still be present at the second mass sensor (50). Output readings or output signals of both mass sensors are taken and these values are used in the calculation of the mass of the natural gas (operation 64). Next, the heat content meter (10), including the chromatographic column (36), are flushed with pure methane (operation 66). Pure methane is preferably used for this process since it is the carrier gas within the chromatographic column and is the comparison gas used in determining the mass of the natural gas (described further below). Then, natural gas is permitted to flow along the second path (29) through the chromatographic column (36) (operation 68). As the gas travels through the chromatographic column, various mixtures are eluted.

First, pure methane is eluted and then, after a short time delay (e.g., 30 seconds) a mixture of nitrogen and methane is eluted (operation 70). These gases pass to the two mass sensors (42) and (50) where the first sensor measures the specific heat of the methane and nitrogen mixture and the second sensor measures the specific heat of pure methane. These values are then used to calculate the mass of the eluted nitrogen and methane mixture (operation 72). Next, the mole fraction of the nitrogen component of said mixture is determined by using the calculated mass of the nitrogen and methane mixture (operation 74).

A mixture of methane, nitrogen and carbon dioxide is eluted (operation 76) next from column (36). This mixture arrives at the first mass sensor (42) as the methane and nitrogen mixture arrives at the second mass sensor (50). Readings or output signals are taken at both mass sensors and these values are used to calculate the mass of the eluted methane, nitrogen and carbon dioxide mixture (operation 78). Next, the mole fraction of the carbon dioxide component of said mixture is determined by using the mass of said mixture (operation 80).

After the above-mentioned measurements and calculations are performed, the results are used to determine the mass of the hydrocarbons in the natural gas (operation 82). Then, the mole fraction of the higher hydrocarbons of the natural gas are calculated (operation 84). This value along with the mole fraction values for the nitrogen and carbon dioxide components are used to determine the mole fraction of the methane content of the natural gas (operation 86).

With the results of the above steps, the heating value of the natural gas is calculated (operation 88).

A particular implementation of the method of the present invention will now be described in detail. Initially, pure methane flows through flow path one in order to flush the mass sensors (42 and 50) with pure methane and the gas flow rate is reduced to zero by ceasing the flow. Then, the mass sensors are balanced by the controller (54) until a zero voltage is attained at the output of the amplifier modules (44). Next, the flow rate of the methane is increased to a desired operating flow rate (e.g., 30 cc per minute) and a reading is taken of each mass sensor output. These outputs are then normalized to unity by multiplying them by a constant $C_1$ or $C_2$ where:

$C_1 = 1/S_{1a}$ and $S_{1a}$ is the initial reading from the first mass sensor; and $C_2 = 1/S_{2a}$ and $S_{2a}$ is the initial reading from the second mass sensor.

The above initialization procedure is employed in order to determine the operating characteristics of the two mass sensors and to ensure the accuracy of those mass sensors.

Referring again to FIG. 1, the operating sequence of the present invention will now be described. After the mass sensors have been flushed with methane, the natural gas is directed to flow along the following path: through filter (15), pressure regulator (14), and two way valve (18). The two way valve (18) will permit the flow of natural gas to the inlet of the three way valve (22). A needle valve (20) connected between valves (18 and 22) will allow slow purging of the natural gas supply line so that the gas at the three way valve inlet is continually representative of the natural gas composition at the source. Three way valve (22) is then used to control the flow of natural gas to the heat content meter (10).

The natural gas will then flow through one way valve (24), needle valve (28), length of tubing (32), three way valve (40) and into mass sensor (42). At this time, the first mass sensor (42) measures the specific heat of the natural gas and the second mass sensor (50) measures the specific heat of methane. The values from these mass sensors are then used to determine the molecular mass of the natural gas. The molecular mass is the mass of one mole of natural gas.

In determining the molecular mass of the natural gas, a comparison is made between the outputs of the two mass sensors. Within these sensors, the characteristics of gas, such as temperature, pressure and flow rate are maintained at the same level so that the difference in the sensor outputs is substantially proportional to the difference in the masses of the two gases. At this point, one of those gases is pure methane, and since the mass of pure methane is known to a high degree of accuracy, this proportionality, which is mathematically depicted below as equation (1), may be used to accurately establish the molecular mass of the natural gas.

$$16.04/mass_{ng} = C_2S_2/C_1S_1 \quad (1)$$

where:
- 16.04 = molecular weight of methane;
- $mass_{ng}$ = mass of natural gas;
- $C_1$ = constant used to normalize the first mass sensor readings to unity;
- $S_1$ = current reading from the first sensor;
- $C_2$ = constant used to normalize the second mass sensor readings to unity; and
- $S_2$ = current reading from the second sensor.

To determine the mass of natural gas, the above proportionality equation may be rewritten as follows:

$$mass_{ng} = 16.04 C_1 S_1 / C_2 S_2 \quad (2)$$

However, to further insure maximum accuracy in the measurement, an instrument amplifier is used with each mass flow sensor. The outputs of both of these amplifiers are referred to a common (midpoint) voltage tap. During the initial calibration (with the pure methane) the outputs of both of the amplifiers are set to zero with no flow and to an optimum positive working value with 30 cc/min of methane flow. During the operation of the device the mass of the gas flowing in each sensor is determined by measuring the voltage between its amplifier output and the common voltage tap. The difference in the masses of the gases flowing in the two sensors is determined by measuring the voltage between the outputs of the two amplifiers. Therefore, equation (2) will be mathematically rewritten in the following manner in order to utilize the differential output.

First, $C_1S_2/C_2S_2$ may be mathematically represented as:

$$C_1S_1/C_2S_2 = C_2S_2/C_2S_2 + C_1S_1/C_2S_2 - C_2S_2/C_2S_2$$

or $$C_1S_1/C_2S_2 = 1 + (C_1S_1 - C_2S_2)/C_2S_2$$

Therefore, equation (2) may be related as follows:

$$mass_{ng} = 16.04 \times (1 + (C_1S_1 - C_2S_2)/C_2S_2)$$

where:
- 16.04 = molecular weight of methane;
- $C_1S_1 - C_2S_2$ = differential output of the two mass sensors; and
- $C_2S_2$ = normalized reading from the second sensor, which is measuring the specific heat of methane at this instance.

Next, the position of three way valves (22 and 40) are changed by the controller (54) so that the methane flows from three way valve (22), through one way valve (26), through needle valve (30), through tubing (34), through five way valve (38), through chromatographic column (36) in a forward direction, back through five way valve (38), through three way valve (40), through first mass sensor (42), through length of tubing (48), and through second mass sensor (50) to the exhaust line. This flow path is maintained for a period of time (e.g., 6 seconds) sufficient to flush out the lines from the outlet of three way valve (22) to the inlet of the chromatographic column. When the lines are flushed, the position of five way valve (38) is changed to allow a reversal of the direction of the flow through the chromatographic column. This flow of methane is maintained until chromatographic column (36) is completely back flushed and the entire flow path from the outlet of three way valve (22) to the exhaust is filled with the methane gas (e.g., 3 minutes).

Then, the position of five way valve (38) is changed to allow a flow in the forward direction through the chromatographic column, and the position of three way valve (22) is changed to provide a flow of natural gas to chromatographic column (36). The specific column selected will elute the various gaseous mixtures in the following order.

First, the column will elute the pure methane which will flow to first mass sensor (42), length of tubing (48) and second mass sensor (50). After a short time delay, (e.g., 30 seconds) the column will elute a mixture of nitrogen and methane. At the time this mixture reaches the first mass sensor (42), the methane will still at the second mass sensor (50). When this occurs, readings will be taken from both sensors, which will be used in the following process.

The molecular mass of the methane and nitrogen mix may be determined as follows:

$$mass_1 = 16.04 \times (1 + (C_1S_1 - C_2S_2)/C_2S_2) \quad (3)$$

where:
- 16.04 = molecular weight of methane;
- $C_1S_1 - C_2S_2$ = differential output of the two mass sensors; and
- $C_2S_2$ = normalized reading from the second sensor, which is measuring the specific heat of methane at this instance.

Then, the mole fraction (i.e., the fractional part of a mole of gas contributed by a constituent of a mixture of gases) of the nitrogen component, N, of the natural gas may be determined from $mass_1$ as follows:

$$N = (mass_1 - 16.04)/11.97 \quad (4)$$

where:
- $mass_1$ = mass of the methane and nitrogen mixture;
- 16 04 = molecular weight of methane; and
- 11.97 = molecular weight of nitrogen minus the molecular weight of methane.

Second, the methane and nitrogen mixture will pass through first mass sensor (42) and length of tubing (48) to second mass sensor (50). By the time said mixture arrives at the second mass sensor, a second mixture composed of nitrogen, methane and carbon dioxide will be eluted from the chromatographic column and passed to first mass sensor (42). This occurs a short time (e.g., 60 seconds) after the natural gas has been introduced to the inlet of the column. As these mixtures pass through the sensors, readings are taken and these readings will be used in determining the mass of the methane, nitrogen and carbon dioxide mixture as follows:

$$mass_2 = mass_1 \times (1 + (C_1S_1 - C_2S_2)/C_2S_2) \quad (5)$$

where:
- $mass_1$ = mass of the methane and nitrogen mixture;
- $C_1S_1 - C_2S_2$ = differential output of the two mass sensors; and $C_2S_2$ = normalized reading from the second sensor, which is measuring the specific heat of the methane and nitrogen mixture at this instance.

Then, the mole fraction of the carbon dioxide component of the natural gas may be determined from $mass_2$ as follows:

$$CO_2 = (mass_2 - mass_1)/(44.08 - mass_2) \quad (6)$$

where:
$mass_2$ = mass of the methane, nitrogen and carbon dioxide mixture;
$mass_1$ = mass of the methane and nitrogen mixture; and
44.08 = molecular weight of carbon dioxide.

After the above-mentioned process is complete, the mass of the hydrocarbon content of the natural gas may be calculated as follows:

$$mass_h = mass_{ng} - 28.01N - 44.08CO_2 \quad (7)$$

where:
$mass_{ng}$ = total mass of the natural gas;
28.01 = molecular weight of nitrogen;
N = mole fraction of the nitrogen component of the natural gas;
44.08 = molecular weight of carbon dioxide; and
$CO_2$ = mole fraction of the carbon dioxide component of the natural gas.

In order to determine the mole fraction of the higher hydrocarbon content of the natural gas (i.e., ethane, propane, butane but not methane) the following calculation will be performed:

$$HHC = (mass_h - 16.04(1 - N - CO_2))/(X - 16.04) \quad (8)$$

where:
$mass_h$ = mass of the hydrocarbon content;
16.04 = molecular weight of methane;
N = mole fraction of the nitrogen component of the natural gas;
$CO_2$ = mole fraction of the carbon dioxide component of the gaseous fuel;
X = weighted mean of molecular weights of ethane, propane, and butane (taken from 49 samples) minus the molecular weight of methane (e.g., 39.776).

After the mole fraction of the higher hydrocarbon content is calculated, the mole fraction of the methane content of the natural gas may be determined as follows:

$$M = 1 - N - CO_2 - HHC \quad (9)$$

where:
N = mole fraction of the nitrogen component of the natural gas;
$CO_2$ = mole fraction of the carbon dioxide component of the natural gas; and
HHC = total mole fraction of ethane, propane and butane.

The heat content (BTU/ft$^3$) of the natural gas may then be determined as follows:

$$BTU = 1016 \times M + Y \times HHC \quad (10)$$

where:
1016 = heat content of a standard cubic foot of pure methane; and
Y = weighted mean of the heat content of a standard cubic foot of ethane, propane and butane (for example 49 samples, a weighted mean of 2301 was obtained).

An apparatus and process for determining the heating value of a continuous flow of a natural gas has been described herein. This particular apparatus and process realizes several advantages. The use of a continuous flow of gas allows the inventive apparatus to be attached directly to a gas pipeline and removes the need for bottling a known amount of gas to be used for measuring. This enhances the ability to have an unattended field operation and reduces the costs of determining the heating value significantly.

Also the use of pure methane as the carrier and comparison gas enhances the reliability of the measurement of the heating value, since the heating value of methane under standard conditions has been laboriously measured to a high degree of accuracy.

Although a preferred embodiment has been depicted and described in detail herein, it will be apparent to those skilled in the relevant art that various modifications, additions, substitutions and the like can be made without departing from the spirit of the invention, and these are therefore considered to be within the scope of the invention as defined by the appended claims.

What is claimed is:

1. An on-line combustionless method for determining the heating value per unit volume of a natural gas which contains at least one noncombustible gas, said method using a chromatographic column having an input and an output, and a first mass sensor and a second mass sensor connected in series to the output of the column, each of the sensors providing an output signal substantially proportional to the mass of the gas at said sensor, said method comprising the steps of:

(a) purging the first mass sensor with a known reference gas;
    (b) introducing the natural gas to the first mass sensor such that said reference gas is transferred to the second mass sensor;
    (c) determining the mass of the natural gas from the output signal of the second mass sensor and the output signal of the first mass sensor;
    (d) purging the chromatographic column with the known reference gas;
    (e) introducing the natural gas to the chromatographic column through its inlet such that said reference gas is expelled from the column as natural gas enters the column;
    (f) waiting a sufficient period of time for a first gas mixture to be eluted from the column and present at the first mass sensor and for said reference gas to be present at the second mass sensor, said first gas mixture containing a first noncombustible natural gas constituent and said reference gas;
    (g) determining the mass of the first mixture from the output signal of the second mass sensor and the output signal of the first mass sensor;
    (h) determining the mole fraction of the first noncombustible natural gas constituent present in the first mixture using the mass of the first mixture determined in step (g) and the molecular weight of the reference gas;
    (i) determining the mass of hydrocarbons present in the natural gas from the mass of the natural gas determined in step (c) and the mole fraction of the first noncombustible natural gas constituent determined in step (h); and (j) determining the heating value of the natural gas from the determined mass of hydrocarbons present in the natural gas.

2. The on-line combustionless method of claim 1, further comprising the steps of:

(k) subsequent said step (f):

(iv) waiting a sufficient period of time for a second gas mixture to be eluted from the column and present at the first mass sensor and for the first gas mixture to be present at the second mass sensor, said second gas mixture containing a second noncombustible natural gas constituent, the first noncombustible natural gas constituent, the reference gas;

(iiv) determining the mass of the second mixture from the output signal of the second mass sensor and the output signal of the first mass sensor; and (iiiv) determining the mole fraction of the second noncombustible natural gas constituent present in the second mixture using the mass of the second mixture and the mass of the first mixture; and wherein said determining step (i) includes:

(l) determining the mass of hydrocarbons present in the natural gas by reference to the mass of the natural gas, the mole fraction of the first noncombustible constituent gas and the mole fraction of the second noncombustible constituent gas.

3. The on-line combustionless method of claim 2 wherein said method includes automatically repeating said steps (a) through (l) in a periodic manner.

4. The on-line combustionless method of claim 2 wherein said reference gas comprises methane, said first noncombustible natural gas constituent comprises nitrogen and said second noncombustible natural gas constituent comprises carbon dioxide.

5. The on-line combustionless method of claim 4 wherein:

(ix) the mass of the natural gas is determined in step (c) from the output signal of the second mass sensor and the differential between the output signal of the first mass sensor and the output signal of the second mass sensor;

(iix) the mass of the first mixture is determined in step (g) from the output signal of the second mass sensor and the differential between the output signal of the first mass sensor and the output signal of the second mass sensor; and (iiix) the mass of the second mixture is determined in step (iiv) from the output signal of the second mass sensor and the differential between the output signal of the first mass sensor and the output signal of the second mass sensor.

6. The on-line combustionless method of claim 5 wherein step (c) includes determining the mass of the natural gas via an algorithm of the form:

$$mass_{NG} = 16.04(1 + (C_1 S_1 - C_2 S_2)/C_2 S_2)$$

wherein:
$mass_{NG}$ = mass of the natural gas;
16.04 = molecular weight of methane;
$C_1$, $C_2$ = constants;
$S_1$ = output signal of the first mass sensor;
$S_2$ = output signal of the second mass sensor.

7. The on-line combustionless method of claim 6 wherein step (g) includes determining the mass of the first mixture via an algorithm of the form:

$$mass_1 = 16.04(1 + (C_1 S_1 - C_2 S_2)/C_2 S_2)$$

wherein:
$mass_1$ = mass of the first mixture;
16.04 = molecular weight of methane;
$C_1$, $C_2$ = constants;
$S_1$ = output signal of the first mass sensor;
$S_2$ = output signal of the second mass sensor.

8. The on-line combustionless method of claim 6 wherein step (h) includes determining the mole fraction of the first noncombustible natural gas constituent via an algorithm of the form:

$$N = (mass_1 - 16.04)/11.97$$

wherein:
$N$ = mole fraction of the first noncombustible constituent, nitrogen;
$mass_1$ = mass of the first mixture;
16.04 = molecular weight of methane;
11.97 = molecular weight of nitrogen minus the molecular weight of methane.

9. The on-line combustionless method of claim 6 wherein step (iiv) includes determining the mass of the second mixture via an algorithm of the form:

$$mass_2 = mass_1(1 + C_1 S_1 - C_2 S_2)/C_2 S_2)$$

wherein:
$mass_2$ = mass of the second mixture;
$mass_1$ = mass of the first mixture calculated in step (g);
$C_1$, $C_2$ = constants;
$S_1$ = output signal of the first mass sensor; and
$S_2$ = output signal of the second mass sensor.

10. The on-line combustionless method of claim 9 wherein step (iiiv) includes determining the mole fraction of the second noncombustible natural gas constituent via an algorithm of the form:

$$CO_2 = (mass_2 - mass_1)/(44.08 - mass_2)$$

wherein:
$CO_2$ = mole fraction of the second noncombustible constituent, carbon dioxide;
$mass_2$ = mass of the second mixture determined in step (iiv);
$mass_1$ = mass of the first mixture determined in step (g); and
44.08 = molecular wight of carbon dioxide.

11. The on-line combustionless method of claim 6 wherein step (i) includes determining the mass of the hydrocarbon gases of the natural gas via an algorithm of the form:

$$mass_h = mass_{ng} - 28.01 N - 44.08 CO_2$$

wherein:
$mass_h$ = mass of the hydrocarbon gases;
$mass_{ng}$ = mass of the natural gas;
8.01 = molecular weight of nitrogen;
$N$ = mole fraction of the first noncombustible constituent, nitrogen;
44.08 = molecular weight of carbon dioxide; and
$CO_2$ = the mole fraction of the second noncombustible constituent, carbon dioxide.

12. The on-line combustionless method of claim 6 wherein the natural gas contains a percentage of higher hydrocarbons, said step (i) further include determining the mole fraction of the higher hydrocarbons from the mass of the natural gas and the mole fractions of the first noncombustible constituent gas and the second noncombustible constituent gas, used in determining the heating value in step (j), and said method includes determining the mole fraction of the higher hydrocarbons present in the natural gas via an algorithm of the form:

$$HHC = (mass_h - 16.04(1 - N - CO_2))/(X - 16.04)$$

wherein:
HHC = higher hydrocarbon content;
$mass_h$ = mass of the hydrocarbon content;
16.04 = molecular weight of methane;
N = mole fraction of the first noncombustible constituent, nitrogen;
$CO_2$ = mole fraction of the second noncombustible constituent, carbon dioxide; and
X = weighted mean of the molecular weights of the higher hydrocarbons.

13. The on-line combustionless method of claim 6 wherein the natural gas contains a percentage of methane and said method includes determining the mole fraction of methane present in the natural gas via an algorithm of the form:

$$M = 1 - N - CO_2 - HHC$$

wherein:
M = mole fraction of methane;
N = mole fraction of the first noncombustible, nitrogen;
$CO_2$ = mole fraction of the second noncombustible constituent, carbon dioxide; and
HHC = higher hydrocarbon content.

14. The on-line combustionless method of claim 6 wherein the method includes determining constant $C_1$ by the steps of:
(xi) purging the first mass sensor with a known gas;
(xii) increasing the flow rate of the known gas to a desired operating flow rate;
(xiii) determining constant $C_1$ via an algorithm of the form:

$$C_1 = 1/S_{1a}$$

wherein:
$C_1$ = first constant; and
$S_{1a}$ = output signal at first mass sensor for the known gas at said desired flow rate.

15. The on-line combustionless method of claim 14 wherein the method includes determining constant $C_2$ by the steps of:
(xvi) allowing the flow described in step (xii) to continue for a sufficient period of time until the known gas is flowing through the second mass sensor at the desired flow rate; and
(xvii) determining constant $C_2$ via an algorithm of the form:

$$C_2 = 1/S_{2a}$$

wherein:

$C_2$ = second constant; and
$S_{2a}$ = output signal at second mass sensor for the known gas at the desired flow rate.

16. The on-line combustionless method of claim 6 wherein step (j) includes determining the heating value of natural gas via an algorithm of the form:

$$BTU = 1016M + Y(HHC)$$

wherein:
BTU = heating value of natural gas;
1016 = heat content of a standard cubic foot of pure methane in BTUs;
M = mole fraction of methane;
Y = weighted mean of the heat content of a standard cubic foot of higher hydrocarbons; and
HHC = higher hydrocarbons.

17. The on-line combustionless method of claim 2 wherein the method includes storing the determined value of step (j).

18. The on-line combustionless method of claim 2 wherein said method includes maintaining the first mass sensor, the second mass sensor and the chromatographic column at the same temperature.

19. The on-line combustionless method of claim 2 wherein said method includes maintaining the pressure of the natural gas and the pressure of the known reference gas constant.

20. An apparatus for use in determining the heating value per unit volume of a natural gas, containing a known gas, which is used as a reference gas, comprising:
(a) a chromatographic column having an inlet and an outlet;
(b) a first mass sensor having an inlet and an outlet, and a second mass sensor having an inlet and an outlet;
(c) first means for alternatively connecting the inlet of said column to one of a source of the known reference gas and a source of the natural gas;
(d) a length of tubing connected between said first mass sensor outlet and to said second mass sensor inlet, said tubing being sized to provide a desired time delay for the arrival of a gas mixture at the second mass sensor;
(e) second means for alternatively connecting said first sensor inlet to one of the source of said known reference gas, the source of the natural gas, and the outlet of said chromatographic column; and
(f) control means for selectively controlling the operation of said first and second means such that gas is determined from output signals of said first and second sensors.

21. The apparatus of claim 20 further comprising instrument amplifiers for determining the differential output of the first mass sensor and the second mass sensor.

* * * * *